（12） United States Patent
Hebert et al.

(10) Patent No.: US 11,904,181 B2
(45) Date of Patent: Feb. 20, 2024

(54) SYSTEMS AND METHODS FOR USE OF A DOSIMETRY APPLICATION SOFTWARE TOOL TO CUSTOMIZE DOSIMETRY AND SPHERE SELECTION FOR RADIOEMBOLIZATION PROCEDURE PLANNING

(71) Applicant: Bard Peripheral Vascular, Inc., Tempe, AZ (US)

(72) Inventors: Casey Tyler Hebert, Tempe, AZ (US); Mark Nicholas Wright, Gilbert, AZ (US); Lee Pusateri, Phoenix, AZ (US); Christopher Basciano, Apex, NC (US); Sivaramakrishnan Balasubramanian, Cary, NC (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 656 days.

(21) Appl. No.: 17/054,569

(22) PCT Filed: May 17, 2019

(86) PCT No.: PCT/US2019/032955
§ 371 (c)(1),
(2) Date: Nov. 11, 2020

(87) PCT Pub. No.: WO2019/222681
PCT Pub. Date: Nov. 21, 2019

(65) Prior Publication Data
US 2021/0154493 A1     May 27, 2021

Related U.S. Application Data

(60) Provisional application No. 62/673,632, filed on May 18, 2018, provisional application No. 62/673,628, filed on May 18, 2018.

(51) Int. Cl.
*A61N 5/10* (2006.01)
*A61K 51/12* (2006.01)

(52) U.S. Cl.
CPC ........ *A61N 5/1031* (2013.01); *A61K 51/1255* (2013.01); *A61N 5/1048* (2013.01); *A61N 2005/1074* (2013.01)

(58) Field of Classification Search
CPC ........ G16H 40/20; G16H 50/50; G16H 40/67; G16H 20/17; G16H 80/00; G16H 40/63;
(Continued)

(56) References Cited

U.S. PATENT DOCUMENTS

| | | |
|---|---|---|
| 4,313,440 A | 2/1982 | Ashley |
| 5,478,323 A | 12/1995 | Westwood et al. |

(Continued)

FOREIGN PATENT DOCUMENTS

| | | |
|---|---|---|
| CN | 105025975 A | 11/2015 |
| DE | 3035290 A1 | 4/1982 |

(Continued)

OTHER PUBLICATIONS

Japanese Office Action dated Apr. 11, 2023 pertaining to Japanese application No. 2020-564537 filed Nov. 17, 2020, pp. 1-6.
(Continued)

*Primary Examiner* — Irakli Kiknadze
(74) *Attorney, Agent, or Firm* — Dinsmore & Shohl LLP

(57) ABSTRACT

Methods and systems for selection of dosimetry levels and sphere amounts of radioactive compounds for use in a radioembolization procedure for procedure planning may include inputting activity parameter information into a dosimetry portal of a dosimetry selection tool; determining a customized activity based on the activity parameter information and one or more customized activity algorithms; generating one or more sphere amount and dosage recom-
(Continued)

mendations based on the customized activity and one or more dosimetry selection algorithms; selecting one of the one or more sphere amount and dosage recommendations as a selected sphere amount and dosage recommendation; and generating a radioactive compound order for the radioembolization procedure based on the customized activity and the selected sphere amount and dosage recommendation.

23 Claims, 13 Drawing Sheets

(58) Field of Classification Search
CPC ........ G16H 20/10; G16H 50/20; A61N 5/103;
A61N 5/1002; A61N 5/1048; A61N
5/1031; A61N 5/1007; A61N 5/1001;
A61N 2005/1074; A61N 2005/1089;
A61N 2005/1019; A61N 5/1037; A61M
5/14566; A61M 39/1011; A61M 39/10;
A61M 25/008; A61M 25/0071; A61M
25/0068; A61M 25/003; A61M 25/0012;
A61M 5/2448; A61M 5/204; A61M 5/19;
A61M 5/1785; A61M 5/16809; A61M
5/1456; A61M 5/14216; A61M 5/1409;
A61M 2205/3327; A61M 2205/3306;
A61M 2039/1027; A61M 2205/502;
A61M 2205/3317; A61M 2039/1033;
A61M 2039/1072; A61M 2205/8206;
A61M 2205/505; A61M 2205/32; A61M
2202/0007; A61M 2025/0681; A61M
2025/0081; A61M 2025/0073; A61M
2025/0042; A61M 2025/0036; A61M
2025/0004; A61M 2005/31598; A61M
2005/247; A61M 2005/2414; A61M
2005/1787; A61K 51/1255; A61K
51/1251; A61K 51/1244; A61B
2018/00529; A61B 34/10; G09B 23/28;
G06T 2210/41; G06T 19/003; G06T
19/20
USPC .......................................................... 378/65
See application file for complete search history.

(56) References Cited

U.S. PATENT DOCUMENTS

| | | | |
|---|---|---|---|
| 5,496,284 A | 3/1996 | Waldenburg | |
| 6,152,913 A | 11/2000 | Feith et al. | |
| 6,222,905 B1 | 4/2001 | Yoda et al. | |
| 6,508,807 B1 | 1/2003 | Peters | |
| 6,606,370 B1 | 8/2003 | Kasprowicz | |
| 6,723,074 B1 | 4/2004 | Halseth | |
| 6,978,286 B2 | 12/2005 | Francis et al. | |
| 7,190,895 B1 | 3/2007 | Groves et al. | |
| 7,630,907 B2 | 12/2009 | Whittacre et al. | |
| 7,668,662 B2 | 2/2010 | Kroll et al. | |
| 7,713,239 B2 | 5/2010 | Uber, III et al. | |
| 8,702,580 B2 | 4/2014 | Hartlep et al. | |
| 9,108,047 B2 | 8/2015 | Agamaite et al. | |
| 9,463,335 B2 | 10/2016 | Griffith et al. | |
| 9,486,643 B2 | 11/2016 | Fox et al. | |
| 9,594,876 B2 | 3/2017 | Sankaran et al. | |
| 9,623,262 B2 | 4/2017 | Vaziri et al. | |
| 9,821,174 B1 | 11/2017 | Fram et al. | |
| 10,092,774 B1 | 10/2018 | Vanderstraten et al. | |
| 10,293,179 B2 | 5/2019 | Carpenter et al. | |
| 10,434,338 B2 | 10/2019 | Sayeed | |
| 10,441,819 B2 | 10/2019 | Sayeed | |
| 10,449,388 B2 | 10/2019 | Yin et al. | |
| 10,478,136 B2 | 11/2019 | Hernandez | |
| 11,043,142 B2 * | 6/2021 | Bova | G09B 23/28 |

| | | |
|---|---|---|
| 2001/0021826 A1 | 9/2001 | Winkler |
| 2002/0095313 A1 | 7/2002 | Haq |
| 2003/0139640 A1 | 7/2003 | Whittacre et al. |
| 2003/0201639 A1 | 10/2003 | Korkor |
| 2004/0111078 A1 | 6/2004 | Miyahara |
| 2004/0143346 A1 | 7/2004 | Francis et al. |
| 2004/0258614 A1 | 12/2004 | Line et al. |
| 2005/0085685 A1 | 4/2005 | Barbut |
| 2005/0101822 A1 | 5/2005 | Whittacre et al. |
| 2006/0033334 A1 | 2/2006 | Weber et al. |
| 2006/0091329 A1 | 5/2006 | Eguchi |
| 2006/0129357 A1 | 6/2006 | Francis et al. |
| 2006/0293552 A1 | 12/2006 | Polsinelli et al. |
| 2007/0129591 A1 | 6/2007 | Yanke et al. |
| 2007/0141339 A1 | 6/2007 | Song et al. |
| 2008/0052317 A1 | 2/2008 | Francis et al. |
| 2008/0058719 A1 | 3/2008 | Edwards et al. |
| 2008/0103564 A1 | 5/2008 | Burkinshaw et al. |
| 2008/0200747 A1 | 8/2008 | Wagner et al. |
| 2009/0018498 A1 | 1/2009 | Chiu et al. |
| 2009/0092677 A1 | 4/2009 | Richard |
| 2009/0232586 A1 | 9/2009 | Diodati et al. |
| 2010/0084585 A1 | 4/2010 | Prosser |
| 2012/0190976 A1 | 7/2012 | Kleinstreuer |
| 2012/0201726 A1 | 8/2012 | Pearcy et al. |
| 2013/0165899 A1 | 6/2013 | Haueter et al. |
| 2013/0317277 A1 | 11/2013 | Lerner |
| 2014/0046295 A1 | 2/2014 | Uber, III et al. |
| 2014/0163302 A1 | 6/2014 | Fox et al. |
| 2014/0207178 A1 | 7/2014 | Chomas et al. |
| 2014/0236093 A1 | 8/2014 | Eggert et al. |
| 2014/0257233 A1 | 9/2014 | Cowan |
| 2015/0178467 A1 | 6/2015 | Britzen et al. |
| 2015/0273089 A1 | 10/2015 | Gray |
| 2015/0285282 A1 | 10/2015 | Weitz et al. |
| 2016/0125154 A1 | 5/2016 | Sankaran et al. |
| 2016/0325047 A1 | 11/2016 | Vedrine et al. |
| 2016/0331853 A1 | 11/2016 | Taub |
| 2016/0331998 A1 | 11/2016 | Hoffman et al. |
| 2017/0021193 A1 | 1/2017 | Griffith et al. |
| 2017/0065731 A1 | 3/2017 | Srinivas et al. |
| 2017/0065732 A1 | 3/2017 | Srinivas et al. |
| 2017/0120032 A1 | 5/2017 | Miyazaki et al. |
| 2017/0151357 A1 | 6/2017 | Cade |
| 2017/0189569 A1 | 7/2017 | Souresrafil et al. |
| 2017/0238951 A1 | 8/2017 | Yang et al. |
| 2017/0304151 A1 | 10/2017 | Van Den Berg et al. |
| 2018/0078313 A1 | 3/2018 | Comaniciu et al. |
| 2018/0169437 A1 | 6/2018 | Carpenter et al. |
| 2018/0214714 A1 | 8/2018 | Carpenter et al. |
| 2018/0236263 A1 | 8/2018 | Borot de Battisti et al. |
| 2019/0299024 A1 | 10/2019 | Carpenter et al. |
| 2020/0108276 A1 | 4/2020 | Yin et al. |

FOREIGN PATENT DOCUMENTS

| | | |
|---|---|---|
| DE | 4318101 A1 | 12/1994 |
| EP | 1083938 B1 | 11/2004 |
| EP | 1523995 A2 | 4/2005 |
| EP | 2179758 A2 | 4/2010 |
| EP | 2575927 A1 | 4/2013 |
| EP | 3010585 B1 | 5/2018 |
| EP | 3344336 B1 | 10/2019 |
| EP | 3384959 B1 | 11/2019 |
| EP | 3103520 B1 | 12/2019 |
| EP | B103521 B1 | 12/2019 |
| EP | 3212287 B1 | 3/2020 |
| FR | 2917981 A1 | 1/2009 |
| JP | 2006017660 A | 1/2006 |
| JP | 2018501045 A | 1/2018 |
| WO | 99062565 | 12/1999 |
| WO | 03019332 A2 | 3/2003 |
| WO | 2007008511 A2 | 1/2007 |
| WO | 2009039203 A2 | 3/2009 |
| WO | 2011014562 A1 | 2/2011 |
| WO | 2011153457 A1 | 12/2011 |
| WO | 2012006555 A1 | 1/2012 |
| WO | 2012118687 A1 | 9/2012 |
| WO | 2013153722 A1 | 10/2013 |

(56) References Cited

FOREIGN PATENT DOCUMENTS

| | | | |
|---|---|---|---|
| WO | 2014040143 | A1 | 3/2014 |
| WO | 2014137980 | A1 | 9/2014 |
| WO | 2014165058 | A1 | 10/2014 |
| WO | 2014205128 | A1 | 12/2014 |
| WO | 2016049685 | A1 | 4/2016 |
| WO | 2016070190 | A1 | 5/2016 |
| WO | 2016161346 | A1 | 10/2016 |
| WO | 2017027879 | A1 | 2/2017 |
| WO | 2017037060 | A1 | 3/2017 |
| WO | 2017053398 | A1 | 3/2017 |
| WO | 2017125443 | A1 | 7/2017 |
| WO | 2017157974 | A1 | 9/2017 |
| WO | 2017197145 | A1 | 11/2017 |
| WO | 2018109733 | A2 | 6/2018 |
| WO | 2019006099 | A1 | 1/2019 |
| WO | 2019016305 | | 1/2019 |
| WO | 2019161135 | | 8/2019 |

OTHER PUBLICATIONS

Intellectual Property Office of Singapore Invitation to Respond to Written Opinion, Search report and Written Opinion dated Jul. 24, 2022, pertaining to Patent Application No. 11202011101Y filed May 17, 2019. p. 1-13.

Chiesa, C. et al.; A dosimetric treatment planning strategy in radioembolization of hepatocarcinoma with 90Y glass microspheres; The Quarterly Journal of Nuclear Medicine and Molecular Imaging, vol. 56, No. 6; Dec. 1, 2012.

Chiesa, C. et al.; Radioembolization of hepatocarcinoma with 90Y glass microspheres: development of an individualized treatment planning strategy based on dosimetry and radiobiology; European Journal of Nuclear Medicine and Molecular Imaging, Springer Verlag, Heidelberg, DE; vol. 42; No. 11; Jun. 27, 2015.

Spreafico, C. et al.; The dosimetric importance of the number of 90Y microspheres in liver transarterial radioembolizaiton (TARE); European Journal of Nuclear Medicine and Molecular Imaging, Springer Verlag, Heidelberg, DE; vol. 41, No. 4; Jan. 30, 2014.

International Search Report and Written Opinion dated Aug. 1, 2019 pertaining to International Application No. PCT/US2019/032983.

International Search Report and Written Opinion dated Dec. 13, 2019 pertaining to International Application No. PCT/US2019/032987.

International Search Report and Written Opinion dated Oct. 16, 2019 pertaining to International Application No. PCT/US2019/032955.

International Search Report and Written Opinion dated Jul. 23, 2019 pertaining to International Application No. PCT/US2019/032950.

International Search Report and Written Opinion dated Sep. 24, 2019 pertaining to International Application No. PCT/US2019/033011.

International Search Report and Written Opinion dated Jul. 26, 2019 pertaining to International Application No. PCT/US2019/032965.

International Search Report and Written Opinion dated Jul. 29, 2019 pertaining to International Application No. PCT/US2019/032954.

International Search Report and Written Opinion dated Aug. 7, 2019 pertaining to International Application No. PCT/US2019/032986.

Arepally, A.; Quantification and Reduction of Reflux during Embolotherapy Using an Antireflux Catheter and Tantalum Microspheres: Ex Vivo Analysis; J Vasc Interv Radiol; 2013; 24:575-580.

Chung, J. et al.; Novel use of the Surefire antireflux device in subtotal splenic embolization; Journal of Vascular Surgery Cases; Dec. 1, 2015; pp. 242-245; vol. 1, No. 4.

Ho, S. et al; Clinical evaluation of the partition model for estimating radiation doses from yttrium-90 microspheres in the treatment of hepatic cancer; European Journal of Nuclear Medicine, Springer, Berlin, Heidelberg, DE: vol. 24. No. 3; Mar. 1, 1997.

Hospital Clinics et al.; Y-90 MicroSpheres (SIRSpheres) for treatment of hepatocellular carcinoma; Mar. 1, 2017.

Morshedi, M. et al.; Yttrium-90 Resin Microsphere Radioembolization Using an Antireflux Catheter: An Alternative to Traditional Coil Embolization for Nontarget Protection; Cardiovasc Intervent Radiol; 2015; 38:381-38; Springer.

Sirtex Medical Limited: Sirtex Medical Products Pty Ltd SIR-Spheres (Ytttrium-90 Microspheres); Apr. 1, 2005.

Theragenics Corp.; Therasphere IDOC TM; Aug. 4, 2015.

Tong, A. et al; Yttrium-90 hepatic radioembolization: clinical review and current techniques in interventional radiology and personalized dosimetry; British Journal of Radiology; vol. 89, No. 1062; Jun. 1, 2016.

US FDA; Theresphere IDOC—Humanitarian Device Exemption (HDE); Sep. 14, 2015.

Westcott, M. et al.; The development, commercialization, and clinical context of yttrium-90 radiolabeled resin and glass microspheres; Advances in Radiation Oncology; 2016; vol. 1; pp. 351-364.

Sirtex Medical Limited; SMAC-SIR-Spheres Microspheres Activity Calculator; May 6, 2018.

Gallio, E. et al.; Calculation of tumour and normal tissue biological effective dose in 90Y liver radioembolization with different dosimetric methods; Physica Medica; Nov. 18, 2016; vol. 32; pp. 1738-1744.

Roberson II, et al. "Factors associated with increased incidence of severe toxicities following yttrium-90 resin microspheres in the treatment of hepatic malignancies", World Journal of Gastroenterology, Article Mar. 14, 2016; 22(10): pp. 3006-3014.

* cited by examiner

FIG. 1

Place an Order — 104, 200A

● Dosimetry ──── ○ Procedure Date and Shipping

Dosimetry Inputs — 202

Lung Shunt Fraction (%LSF)
[ 2% ]

Anticipated Residual Waste (%)
[ 1% ]

Previous Dose to the Lungs (Gy)
[ 0 ]

Desired Dose to Liver (Gy)
[ 200 ]

Target Liver Volume (cc)
[ 300 ]

[ Calculate ] — 204

MIRD Calculation — 206

Target Liver Mass (kg)
[ 0.31 ]

Activity at Administration (GBq)
[ 1.27 ]

Calculated Dose to Lungs (Gy)
[ 1.26 ]

Dose Limit to Lungs (Gy)
[ 30 ]

Cumulative Dose to Lungs (Gy)
[ 1.26 ]

Cumulative Dose Limit to Lungs (Gy)
[ 50 ]

Order Details — 208

Based on your inputs, our recommendations for this order are:
- Dosage of 3 million spheres with activity of 425 Bq/Sphere -or-
- Dosage of 5 million spheres with activity of 255 Bq/Sphere Sphere Selection         Activity Per Sphere (Bq/Sphere)
[ Select one ▾ ]         [        ]

Activity to Be Ordered (GBq)
[ 1.27 ]

OPTIONAL-% Dose Modification (e.g. -10%)
[        ]

OPTIONAL-Split Dose Across Vials (max 3)
Vial 1 (%)   Vial 2 (%)   Vial 3 (%)
[        ]   [        ]   [        ]

[ Review Order ] — 210

Dosimetry Portal

Home | Place an Order | 104 | Order History | Review Orders

○ Dosimetry    ○ Procedure Date and Shipping

Place an Order — 212

Order Details — 214

Activity to Be Ordered
1.27 GBq

Sphere Selection
3 Million

Activity Per Sphere
425 Bq/Sphere

% Dose Modification
0%

Patient Target Dose
200 Gy

Dosimetry Inputs — 216

Lung Shunt Fraction
2%

Anticipated Residual Waste
1%

Previous Dose to the Lungs
0

Desired Dose to the Liver
200 Gy

Target Liver Volume
300 cc

MIRD Calculation — 218

Target Liver Mass
0.31 kg

Activity at Administration
1.27 GBq

Calculated Dose to Lungs
1.26 Gy

Dose Limit to Lungs
30 Gy

Cumulative Dose to Lungs
1.26 Gy

Cumulative Dose Limit to Lungs
50 Gy

220 — Back        222 — Confirm Order Details

| MIRD Dosimetry Info | | |
|---|---|---|
| Time Zone (Drop Down) | (UTC-7:00) Mountain Stan | ~200B |
| Treatment Date (MM/DD/YYYY) | 10/28/2018 | |
| Treatment Time (Drop Down) | 10:00 AM | |
| Lung Shunt Fraction (%LSF) | 3% | |
| Anticipated Residual Waste (%) | 2% | |
| Previous Dose to the Lungs (Gg) | 0 | |
| Desired Dose to Liver (Gg) *Dose to perfused liver volume | 80 | |
| Target Liver Volume (cc) *Perfused liver volume exposed to Y | 1600 | |

250 — Advanced Dosimetry

| | MIRD Calculation | |
|---|---|---|
| Target Liver Mass (kg) | 1.65 | Dosimetry Guidance |
| Activity at Administration (GBq) | 2.77 | |
| Calculated Dose to Lungs (Gg) | 4.08 | |
| Dose Limit to Lungs (Gg) | 30 | |
| Cumulative Dose to Lungs (Gg) | 4.08 | |
| Cumulative Dose Limit to Lungs | 50 | |
| OPTIONAL - % Dose Modification | 0% | |
| Activity to be Ordered (GBq) | 2.77 | |
| | | :andard Activity/Sphe |
| d Number of Spheres (REFERENCE) | 9 Million | 300 Bq/Sphere |
| Sphere Selection (Drop Down - R | 7.5 Million | 370 Bq/Sphere |
| Activity and Sphere Selection Not (e.g. -Reduced activity due to previous chemo treatments- | | |

| order | Final Order Details | |
|---|---|---|
| | Patient Target Dose (Gg) | 80 |
| | Required Activity at Treatment | 2.77 |
| | Number of Spheres | 7.5 Million |
| | Bq per Sphere (Reference) | 370 |
| | Date of Delivery (MM/DD/YYY | |

MIRD Dosimetry Info — 252

| Field | Value |
|---|---|
| Target Liver Volume (cc) | 0 |
| Desired Dose (Gy) | 0 |
| Time Zone (Drop Down) | |
| Treatment Date (MM/DD/YYYY) | 1/0/1900 |
| Treatment Time (Drop Down) | |
| Lung Shunt Fraction (%LSF) | 0% |
| Anticipated Residual Waste (%) | 0% |
| Previous Dose to the Lungs (Gy) | 0 |

BSA Dosimetry Info — 254

| Field | Value |
|---|---|
| Total Liver Volume (cc) | 0 |
| Patient height (cm) | 0 |
| Patient weight (kg) | 0 |
| Target Tumor Volume (cc) | 0 |

— 256

Partition Dosimetry Info

| Field | Value |
|---|---|
| Target Dose to Tumor (Gy) | 0 |
| T/N Ratio | 0 |
| Lung Mass (kg) | 0 |
| Total Liver Mass (g) | 0 |
| Healthy Liver Mass (g) | 0 |
| Target Tumor Mass (g) | 0 |

|  | MIRD Calculate — 262 | BSA Calculate — 264 | Partition Calculate — 266 |
|---|---|---|---|
| Target Liver Mass (kg) | 0.000 | 0.0000 | 0.0000 |
| Activity at Administration (GBq) | 0.00 | #DIV/0! | #DIV/0! |
| Calculated dose to lungs (Gy) | 0.00 | | #DIV/0! |
| Dose limit to lungs (Gy) | 30 | 30 | 30 |
| Cumulative dose to lungs (Gy) | 0.00 | #DIV/0! | #DIV/0! |
| Cumulative dose limit to lungs (Gy) | 50 | 50 | 50 |

BACK

| | 262 MIRD Calculate | 264 BSA Calculate | 266 Partition Calculate |
|---|---|---|---|
| Target Liver Mass (kg) | 0.000 | 0.0000 | 0.000 |
| Activity at Administration (GBq) | 0.00 | #DIV/0! | #DIV/0! |
| Calculated dose to lungs (Gy) | 0.00 | #DIV/0! | #DIV/0! |
| Dose limit to lungs (Gy) | 30 | 30 | 30 |
| Cumulative dose to lungs (Gy) | 0.00 | #DIV/0! | #DIV/0! |
| Cumulative dose limit to lungs (Gy) | 50 | 50 | 50 |

Optional Select Treatment Type  270  #N/A  Bq/sphere

Optional Recommended Number of Spheres  272  #VALUE!  Million

Sphere Selection (Drop Down)  Million

Activity Selection (Drop Down)  q

% Dose Modification (e.g. -%10)  0%

Required Activity  #VALUE!  GBq

274

278  Final Order Details  276

ORDER

Patient Target Dose (Gy)  0

Required Activity at Treatment (GBq)  #VALUE!

Number of Spheres  0  Million

GBq per sphere (Reference)  #VALUE!

Date of Delivery  3/20/2018

FIG. 8

Y90 ORDER FORM 280

Phone:

Please Fax or Email
Y90 Order Form and
Treatment Plan (if applicable):

FAX:                    or

ATTN To:
Facility Name:
Address:
City, State, Zip:
Person Placing Order:
Phone Number:
Special Comments:

Patient Name:
Physician Name:
Purchase Order Number:

Billing (Check One)
☐ Bill to
☐ ame as above

CONFIDENTIAL-- WORKSHEET IS FOR REFERENCE ONLY. NOT FOR CLINICAL USE.

| | |
|---|---|
| Order Date: | 5/9/2019 |
| Time Zone: | Not Specified |
| Treatment Date: | 1/0/1900 |
| Treatment Time: | Not Specified |
| Treatment Activity Required: | #VALUE! |
| Number of Spheres: | Not Specified |
| Delivery Date: | 3/20/2018 |

If activity is to be split over multiple vials, please specify split below:

| Optional: | Vial | 1 | 2 | 3 | Total |
|---|---|---|---|---|---|
| | Enter Percent | 100% | 0% | 0% | 100% |
| | Acitivity (GBq) | #VALUE! | #VALUE! | #VALUE! | #VALUE! |

Approve Order 300

Patient Information

Medical Record Number
[ 2813318004 ]

Lung Shunt Fraction ⓘ
[ 3 ] (%LSF)

Anticipated Residual Waste ⓘ
[ 2 ] %

Previous Dose to the Lungs ⓘ
[ 0 ] Gy

Desired Dose ⓘ
[ 80 ] Gy

Targeted Liver Volume ⓘ
[ 1600 ] cc

Targeted Liver Mass
[ 165 ] kg

Sphere Selection
[ 40 Million ▼ ]

Optional - % Dosage Modification (e.g -10%)
[ 0 ] %

Scheduling

Date & Time of Operation
[ 12/3/2018 9:00AM ] 📅

Time Zone
[ UTC-4:00 Atlantic Standard Time ▼ ]

Street Address
[ 1 Begton Drive, Franklin Lakes 07417 ]

State
[ New Jersey ▼ ]

Zip Code
[ 07470 ]

Contact email
[ pocAdmin@bd.com ]

Dosimetry Outputs

Activity of Administration
[ 2.77 ] GBq

Calculated Dose to Lungs
[ 4.08 ] Gy

Dose Limit to Lungs
[ 30 ] Gy

Cumulative Dose to Lungs
[ 4.08 ] Gy

Cumulative Dose Limit to Lungs
[ 50 ] Gy

| Activity to be Ordered | Standard Activity/Sphere |
|---|---|
| [ 2.77 ] GBy | [ 69 ] Bq/Sphere |
| Recommended Number of Spheres | Standard Activity/Sphere |
| [ 2 ] Million | [ 300 ] Bq/Sphere |

Split dose over multiple Vials

Order Status

[ Needs Approval ▼ ]

[ Save ]  302

FIG. 10

Order History 400

Filter By order Status

All ▼

404

| Order Number | MRN | Procedure Date | Order Date | Activity | Number of Spheres | Status | Tracking Number |
|---|---|---|---|---|---|---|---|
| xxxx7 | 2813348004 | 12/3/18 10:35AM | 11/06/18 | 2.87 GBq | 15M | Needs Update | |
| xxxx6 | 8104459367 | 12/1/18 9:05AM | 10/7/18 | 3.01 GBq | 10M | Needs Approval | |
| xxxx5 | 7944582178 | 10/15/18 9:00PM | 10/02/18 | 2.77 GBq | 40M | Needs Fulfillment | |
| xxxx4 | 8104459867 | 11/30/18 2:00PM | 10/08/18 | 2.12 GBq | 10M | Order Processing | |
| xxxx3 | 1012217894 | 11/25/18 10:35AM | 10/12/18 | 3.22 GBq | 10M | In Transit | 2582410857254566 |
| xxxx2 | 8133798967 | 11/12/18 11:45AM | 10/11/18 | 2.98 GBq | 5M | Delivered | 9202410857254566 |
| xxxx1 | 5554747102 | 10/28/18 1:00PM | 10/12/18 | 2.81 GBq | 3M | Delivered | 3771012836115901 |

402

Contact US | Call 1-800-BD-HELPS or contact your local Sales Rep

FIG. 11

SYSTEMS AND METHODS FOR USE OF A DOSIMETRY APPLICATION SOFTWARE TOOL TO CUSTOMIZE DOSIMETRY AND SPHERE SELECTION FOR RADIOEMBOLIZATION PROCEDURE PLANNING

CROSS-REFERENCE TO RELATED APPLICATIONS

The present application claims the benefit of U.S. Provisional Pat. App. No. 62/673,628, entitled "DUAL-STAGE SYRINGES WITH LOCKING MECHANISM," and filed on May 18, 2018, and U.S. Provisional Pat. App. No. 62/673,632, entitled "RADIOEMBOLIZATION DELIVERY DEVICE," and filed on May 18, 2018, the entireties of which are incorporated by reference herein.

TECHNICAL FIELD

The present specification generally relates to procedure planning utilizing medical devices for treating cancer, and more particularly to procedure planning utilizing medical devices configured and operable to deliver radioactive compounds to a treatment area within a patient's body in procedures such as transarterial radioembolization and determination of customized dosimetry and sphere selection of the radioactive compounds for use in such radioembolization delivery devices.

BACKGROUND

In cancer treatments involving radiation therapy, inadvertent or excess exposure to radiation from radioactive therapeutic agents can be harmful and potentially lethal to patients or medical personnel. Accordingly, medical instruments for radiation therapies must be configured to localize the delivery of radioactive material to a particular area of the patient's body while shielding others from unnecessarily being exposed to radiation.

Transarterial radioembolization is a transcatheter intra-arterial procedure performed by interventional radiology and is commonly employed for the treatment of malignant tumors. During this medical procedure, a microcatheter is navigated into a patient's liver where radioembolizing microspheres loaded with a radioactive compound, such as yttrium-90 ($^{90}Y$), are delivered to the targeted tumors. The microspheres embolize blood vessels that supply the tumors while also delivering radiation to kill tumor cells.

Generally, medical devices for performing radioembolization procedures require multiple syringes, external tubing, a vial containing the radioactive compound, and a bulky shield assembly for containing and shielding the radioactive vial. Such devices typically involve time consuming and labor-intensive setup procedures. The complex devices are commonly stationary and thereby limit a physician's mobility in an operating room to within a certain proximity of the device.

Routine manipulation of a product container storing radioactive material during radioembolization procedures generally requires a Nuclear Medicine Technician, who handles the material with forceps or tweezers. This process involves further potential of exposing additional medical personnel to radioactivity, and contaminating the operating room. Syringes for manually administering the radioactive compound as an administered fluid are prone to inconsistent flow rates and pressures. Insufficient injection rates result in decreased bead dispersion, which may impact efficacy of the treatment.

Accordingly, a need exists for a tool to determine efficient amounts of radioactive compounds to administer to a patient through a simplified medical device that is configured and operable to perform radioembolization.

SUMMARY

In one embodiment, a method that is computer-implemented for selection of dosimetry levels and sphere amounts of radioactive compounds for use in a radioembolization procedure for procedure planning may include inputting activity parameter information into a dosimetry portal of a dosimetry selection tool, determining, via a processor, a customized activity based on the activity parameter information and one or more customized activity algorithms, and generating one or more sphere amount and dosage recommendations based on the customized activity and one or more dosimetry selection algorithms. The method may further include selecting one of the one or more sphere amount and dosage recommendations as a selected sphere amount and dosage recommendation, and generating, via the processor, a radioactive compound order for the radioembolization procedure based on the customized activity and the selected sphere amount and dosage recommendation.

In another embodiment, a system for selection of dosimetry levels and sphere amounts of radioactive compounds for use in a radioembolization procedure for procedure planning may include a dosimetry selection tool including a dosimetry portal and a graphical user interface, and a processor communicatively coupled to a dosimetry selection tool and a non-transitory computer storage medium. The non-transitory computer storage medium may store instructions that, when executed by the processor, cause the processor to: receive, via the graphical user interface, an input of activity parameter information into the dosimetry portal of the dosimetry selection tool, determine, via the processor, a customized activity based on the activity parameter information and one or more customized activity algorithms, and generate, via the processor, one or more sphere amount and dosage recommendations based on the customized activity and one or more dosimetry selection algorithms. The instructions may, when executed by the processor, further cause the processor to receive, via the graphical user interface, a selection of one of the one or more sphere amount and dosage recommendations as a selected sphere amount and dosage recommendation, and generate, via a processor, a radioactive compound order for the radioembolization procedure based on the customized activity and the selected sphere amount and dosage recommendation.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 1 illustrates a home page screen view of a graphical user interface (GUI) of a dosimetry portal of a dosimetry selection tool for radioembolization procedure planning, according to one or more embodiments shown and described herein;

FIG. 2 illustrates an order page screen view of the dosimetry portal of FIG. 1 to submit one or more dosimetry inputs and select order details based on dosimetry and sphere recommendations, according to one or more embodiments shown and described herein;

FIG. 3 illustrates a review order page screen view of the dosimetry portal of FIG. 1, according to one or more embodiments shown and described herein;

FIG. 4 illustrates a confirm order page screen view of the dosimetry portal of FIG. 1 to input procedure and shipping information, according to one or more embodiments shown and described herein;

FIG. 5 illustrates a confirm order page screen view of the dosimetry portal of FIG. 1 to assign shipping information input to appropriate review personnel, according to one or more embodiments shown and described herein;

FIG. 6 illustrates another, basic order page screen view of the dosimetry portal of FIG. 1 to submit one or more dosimetry inputs and select order details based on dosimetry and sphere recommendations on a basic screen including one activity customization algorithm, according to one or more embodiments shown and described herein;

FIG. 7 illustrates a first part of another, advanced order page screen view of the dosimetry portal of FIG. 1 to submit one or more dosimetry inputs and select order details based on dosimetry and sphere recommendations on an advanced screen including three different activity customization algorithms, according to one or more embodiments shown and described herein;

FIG. 8 illustrates a second part of the advanced order page screen view of FIG. 7 to show treatment, dose, and sphere selection information, according to one or more embodiments shown and described herein;

FIG. 9 illustrates an order form screen view of the dosimetry portal of FIG. 1, according to one or more embodiments shown and described herein;

FIG. 10 illustrates an approve order screen view of the dosimetry portal of FIG. 1, according to one or more embodiments shown and described herein;

FIG. 11 illustrates an order history screen view of the dosimetry portal of FIG. 1, according to one or more embodiments shown and described herein;

DETAILED DESCRIPTION

Figure 12:
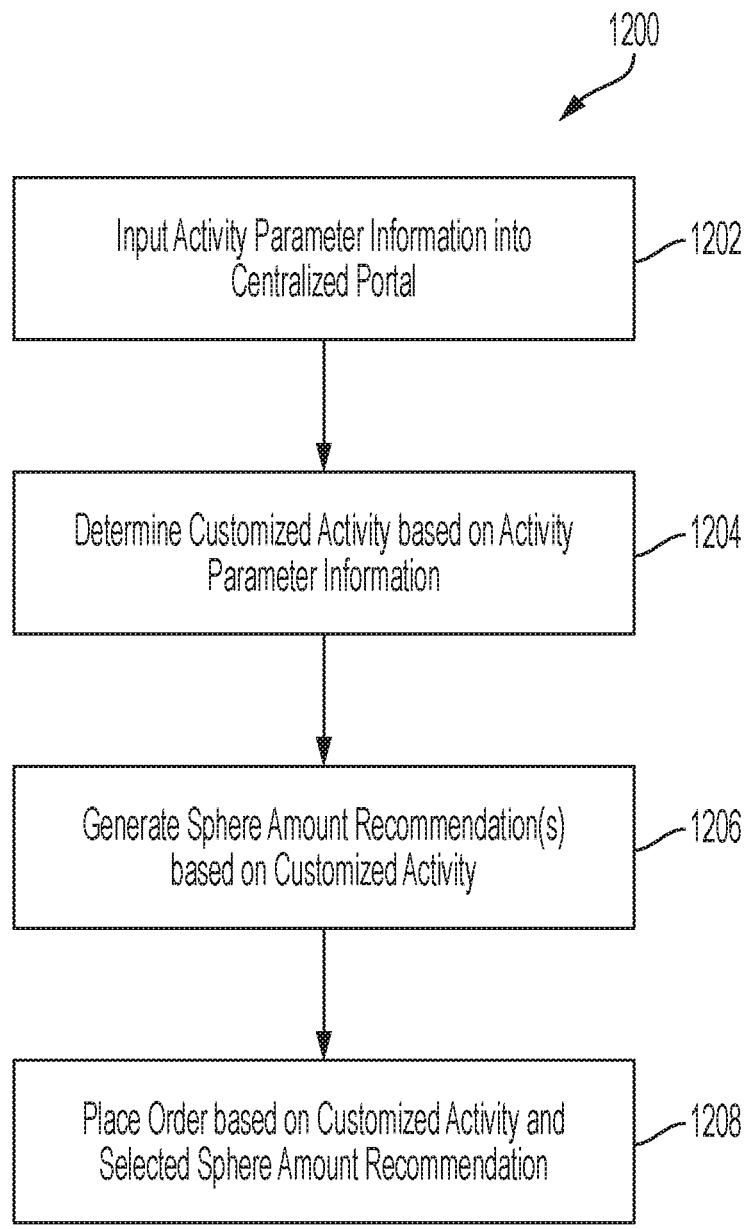
FIG. 12 is a flow chart of a process utilizing the dosimetry portal screens of FIGS. 1-11, according to one or more embodiments shown and described herein.

Referring generally to the figures, embodiments of the present disclosure are directed to systems and methods for selection of dosimetry levels and sphere amounts of radioactive compounds for use in a radioembolization procedure for procedure planning as described herein. Various embodiments of such systems and methods are described in detail herein.

The present disclosure is directed to a centralized portal as a software application tool utilized across platforms, such as web-based to mobile applications, to determine a radioactivity and number of spheres to order for a Yttrium-90 (Y90) radioembolization procedure. A patient being planned for radioembolization will typically undergo several rounds of imaging to determine a location, size, shape, vascularity, uptake of the tumor, and/or shunting of particles (e.g., spheres) to other organs. The determined information is then used to calculate a required radioactive dose at the time of treatment. Current dosimetry models may include a MIRD, Body Surface Area (BSA) model, Partition model, or modified versions to make this determination, which may be used through mobile applications, online applications, and/or spreadsheets for model evaluation. However, this creates a disjointed process requiring extra physician steps decentralized from the model platforms and less ease of hospital coordinate logistics with respect to ordering based on the determined required radioactive dose. Further, market suppliers tend to control dosages based on a pre-set activity per sphere. In current dosimetry models, the model steps are performed separately and individually such that results are collated manually for comparison to the controlled dosage, which increases delays in procedure planning in contrast to one or more technical effect of the one or more models of this disclosure to vary dosage selections per patient and to reduce delays in procedure planning.

As an example, SIRTeX spheres have an activity of 50-80 Bq/sphere and BTG spheres are approximately 2500 Bq/sphere. Becquerel (Bq) is a unit of radioactivity defined as the activity of a quantity of radioactive material in which a nucleus decays per second. Consequences of such pre-set activities per sphere may include suppliers having to increase the ordered doses more than a physician prescribes to allow the orders to age and decay down to a desired dose, which results in an extended delivery time and extraneous use of materials, and physicians are not presented with an option to prescribe a number of sphere and a dosage per sphere as increasing a number of spheres for pre-set activities per spheres would simply increase a total dose. Physicians instead tend to order even higher does than needed to accommodate a desire for a number of spheres and further extend the radioactivity decay and delivery time.

A dosimetry selection software application tool as described herein is configured to act as a centralized platform that allows physicians and users to prescribe and select both a dosage and a number of spheres desired to deliver to a patient for a radioembolization procedure. Through the dosimetry selection software application tool, users may simultaneously evaluate multiple dosimetry models along with one or more dosimetry selection algorithms to determine an appropriate number of spheres to order with a selected dosage per sphere for a radioembolization procedure. The dosimetry selection software application tool may utilize one or more algorithms based on prior treatments and/or specific procedure strategies or procedure locations. Further, to aid with ease of hospital logistics and processing, the selected order information may be directly translated to an order form as well as other clinical documentation. The dosimetry selection software application tool may include a notification and/or tracking system to allow for internal and/or external personnel use, such as with respect to a hospital, of the systems and portals described herein.

Figure 1:
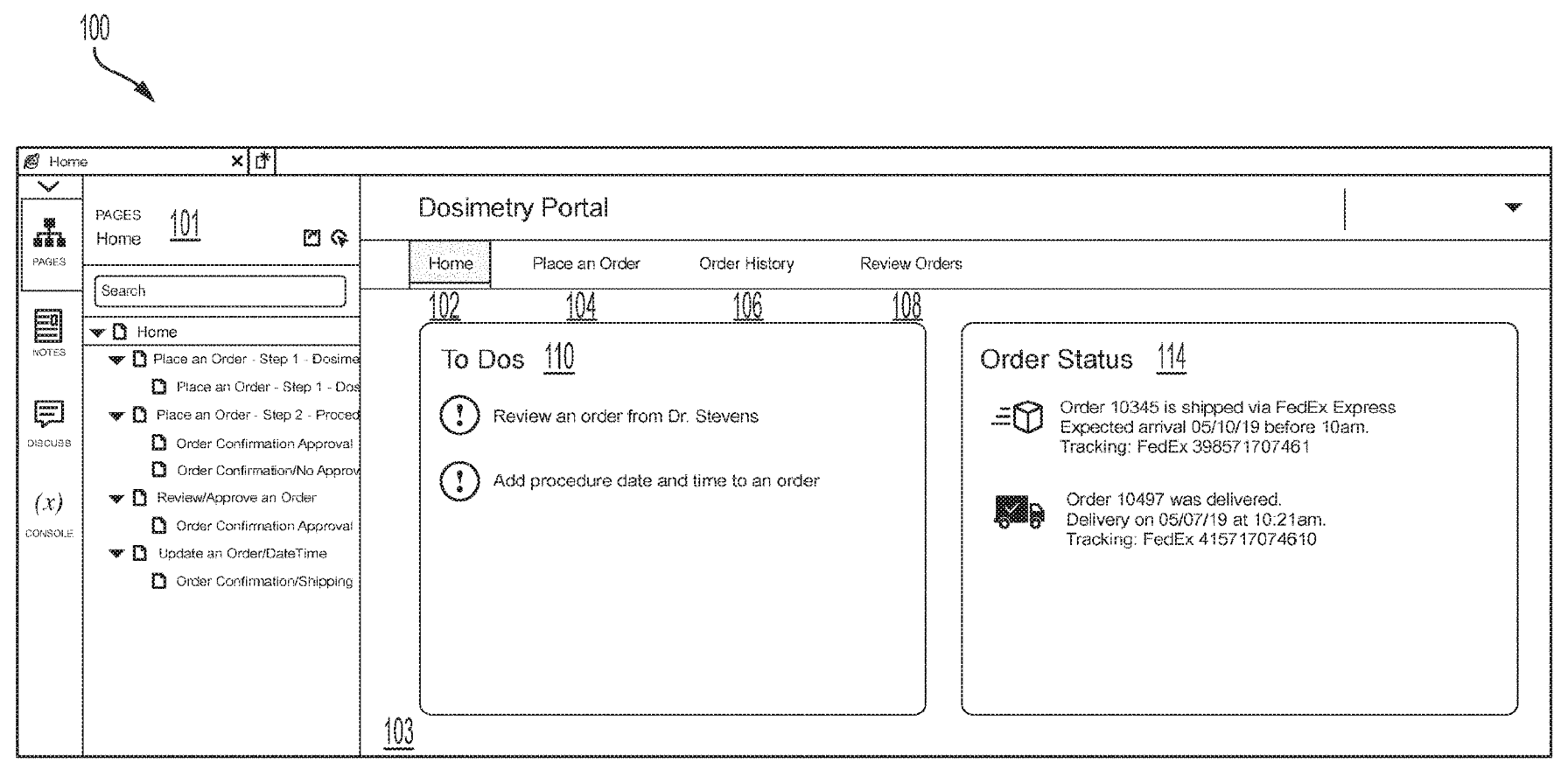

Referring to FIG. 1, a home page screen 103 is shown of a dosimetry portal 100 of a dosimetry selection tool 1312 including a graphical user interface (GUI) 1326 (FIG. 13) for radioembolization procedure planning, which is described in greater detail further below. The dosimetry portal includes a navigation menu 101 to navigate to a desired screen of the dosimetry portal 100 through selection of a menu navigation option. The dosimetry portal further includes, for navigation to respective screens, a home tab 102, a place an order tab 104, an order history tab 106 such that a user may review the histories of one or more orders, and a review orders tab 108 such that a user may review, update, and/or approve one or more saved orders. The home page screen 103 illustrates a To Dos sub-screen 110, including a list of items to accomplish for a user of the dosimetry portal 100. By way of example, and not as a limitation, the To Dos sub-screen 110 of FIG. 1 includes a listing of tasks for the signed in user specific to the user of (1) review an order from Dr. Stevens and (2) add a procedure date and time to an order. The home page screen 103 further illustrates an Order Status sub-screen 114 including a listing of one or more order status to which the signed in user has access rights to view.

In embodiments, the dosimetry portal 100 may include a sign in (e.g., log in) for one or more users for user specified portal usage, data security, and/or data collaboration. The dosimetry portion 100 may thus include a security feature to permit one or more users to access one or more different levels of the dosimetry portal 100 based on user assigned access rights. A first user may have access to a specific set of GUI screens of the dosimetry portion 100 based on a basic security clearance level, while a second user may have access to another specific set of GUI screens of the dosimetry portion 100 including more screens than the first user has access to based on an advanced security clearance level. It is to be understood that different levels of security clearance assigning one or more users corresponding different levels of access rights to GUI screens and permissions with respect to the dosimetry portion 100 are contemplated and within the scope of this disclosure.

Further, a first user may select another user to review and approve an order in the dosimetry portion 100, or the dosimetry portion 100 may be configured to automatically assign the order for review and approval by another user after the first user has generated a first order draft. As a non-limiting example, the first user with the basic security clearance level may be permitted to input an order and generate the first order draft as described herein. The first user may assign the first order draft to a second user with the advanced security clearance level for review and approval, or the dosimetry portion 100 may be configured to place the first order draft into an review order approvals GUI listing one or more orders for approval by the second user and/or notify the second user that the first order draft is ready for review and approval by the second user.

In embodiments, the dosimetry portion 100 is configured to provide a data collaboration platform such that one or more orders may be created, edited, viewed, approved, and/or placed by a plurality of users have one or more levels of security clearance and user specific access rights to the one or more orders as described herein. Thus, multiple users may be able to view and/or review an order as well as historical data of a plurality of orders to aid with, for example, ease of hospital logistics in sharing, reviewing, and submitting such orders in a centralized platform.

Referring to FIG. 2, an order page screen 200A is shown. The order page screen 200A is accessible through the place an order tab 104 of FIG. 1, for example. The order page screen 200A includes a Dosimetry Inputs sub-screen 202, a customized activity algorithm sub-screen 206, and an Order Details sub-screen 208. Activity parameter information may be input into the dosimetry portal 100 in embodiments described herein, where such activity parameter information may include information used to estimate a dosage activity using one or more models and/or algorithms as described herein. As a non-limiting example, the Dosimetry Inputs sub-screen 202 includes fields to input one or more of the following activity parameter information inputs: (1) lung shunt fraction (LSF) as a percentage value, (2) anticipated residual waste as a percentage value, previous dose to the lungs in units of Gray (Gy), which is a derived unit of ionizing radiation defined as the absorption of one joule of radiation energy per kilogram of matter, (3) desired dose to liver in units of Gy, and (4) target liver volume as tissue volume in units of cubic centimeter (cc). As a non-limiting example, the Dosimetry Inputs sub-screen 202 of FIG. 2 incudes a % LSF of 2%, an anticipated residual waste of 1%, a previous dose to the lungs of 0 Gy, a desired dose to liver of 200 Gy, and target liver volume of 300 cc. The activity parameter inputs may further include a time zone, a treatment date, a treatment time, patient specific parameters, prior treatment information, and/or the like. The Dosimetry Inputs sub-screen 202 further includes a calculate button 204 to calculate a customized activity based on the activity parameter information inputs and a customized activity algorithm. As described herein, the customized activity is an amount of radioactivity for spheres that may be variable such that different amount of spheres options may each include respective radioactivity per sphere levels to each obtain a total customized activity level, which different amount of sphere options are generated based on associated customized activity algorithms as described herein.

As a non-limiting example, the customized activity algorithm sub-screen 206 includes a MIRD dosimetry calculation algorithm to determine a customized activity based on the inputs from the Dosimetry Inputs sub-screen 202. As a non-limiting example, based on the inputs in the Dosimetry Inputs sub-screen 202 of FIG. 2, the MIRD dosimetry calculation of the customized activity algorithm sub-screen 206 includes a target liver mass of 0.31 kg, an activity at administration value of 1.27 GBq (e.g. as a customized activity), a calculated dose to lungs of 1.26 Gy, a dose limit to lungs of 30 Gy, a cumulative dose to lungs of 1.26 Gy, and a cumulative dose limit to lungs of 50 Gy. It is to be understood that any dosimetry calculation algorithms as known or as yet-to-be developed may be used by the dosimetry portal 100 and within the scope of the disclosure. The dosimetry calculation algorithms as customized activity algorithms described herein may include a MIRD dosimetry calculation algorithm, a BSA dosimetry calculation algorithm, or a Partition dosimetry calculation algorithm as known to one of ordinary skill in the art.

The Order Details sub-screen 208 includes one or more sphere amount and dosage recommendations based on the customized activity and a utilized dosimetry selection algorithm, such as the MIRD dosimetry calculation algorithm of FIG. 2. Displaying of different recommendations from different models allows the compared different recommendations to be directly compared by a user, and further displaying of results in a same format assists a user when deciding between recommendations from one or more models to select. In embodiments, one or more dosimetry selection algorithms to generate the one or more sphere amount and dosage recommendations may include an activity-per-sphere algorithm, an activity based on embolic load algorithm, or combinations thereof. The activity-per-sphere algorithm may include a division of the customized activity with a predetermined amount of spheres per activity unit, such as 300 Bq/sphere. As a non-limiting example, a customized activity of 3 gigabecquerel (GBq) divided by 300

Bq/sphere results in 10,000,000 spheres at 300 Bq/sphere. In embodiments, outputting model results in a format of number of spheres with number of Bq/sphere provides immediate, real-time clarity to a user as to what the possible order options are in contrast to current dosimetry models in which model results are converted in an order manually by a user by comparing model outputs to a fixed activity of supplier spheres.

Alternatively, the activity based on embolic load algorithm may include use of a tissue volume input and a predetermined embolic load determination per cubic centimeter of tissue such that the spheres and dosage amount determination is a function of embolic load. A non-limiting embolic load example of how many spheres one cubic centimeter of tissue may handle may be, for example, 20,000 spheres/cc. Thus, a tissue volume of 300 cc would yield a calculation of 6,000,000 spheres. A user may adjust an amount of spheres achieving a customized activity, such as to reduce the amount of spheres such that each sphere includes a greater amount of radioactivity to achieve the total customized activity level, or to increase the amount of spheres such that each sphere includes a lower amount of radioactivity to achieve the total customized activity level. In embodiments, a user may select 3 million spheres to achieve a total customized activity level of 1.27 from the Order Details sub-screen 208 at 425 Bq/sphere, or the user may select a greater amount of 5 million spheres to achieve the total customized activity level of 1.27 from the Order Details sub-screen 208 at a reduced dosage per sphere of 255 Bq/sphere. The user may select from a drop down sphere selection amount between 1 million spheres to 40 million spheres to achieve the total customized activity level (e.g., of 1.27 in FIG. 2). In embodiments, the user may be presented with up to thirteen options ranging from between and including 1 million spheres to 40 million spheres.

As a non-limiting example, the dosimetry selection algorithm may provide for the values of FIG. 2 a recommendation of a dosage of 3 million spheres with a radioactive activity of 425 Bq/Sphere along with an alternative recommendation of 5 million spheres with activity of 255 Bq/Sphere such that more spheres with a reduced amount of activity are used in the alternative recommendation. It is to be understand that the physical size of the spheres, also referenced as microspheres, do not change though different amounts of spheres at different dosage levels may be ordered to meet a customized activity value and to vary amount of radioactivity across the ordered spheres per sphere. In embodiments, however, the dosimetry portal 100 may include provide a GUI providing size and/or size distribution information as generated by a size determination algorithm. Manufacturers may use such information to manufacture the ordered spheres of varying size, distribution, activity, and/or amount based on manufacturer sphere production processes.

The user may further use the Order Details sub-screen 208 to modify the dosage, such as to increase by +10% or to decrease by −10%. In embodiments, the modification may be input as a fractional amount rather than a percentage amount. Additionally or alternatively, the user may split the dose across vials, such as up to a maximum of three vials to achieve a total 100% dosage amount. Thus, the dosage amounts may be varies across up to three tissue areas of different radioactive sensitivities, or across three blood vessels feeding a tumor requiring up to three different radioactive dosing levels to achieve the total customized activity value to treat the tumor during the radioembolization procedure. A review order button 210 allows a user to review an order on a review order page 212 of FIG. 3.

Referring to FIG. 3, the review order page 212 includes an Order Details sub-screen 214, a Dosimetry Inputs sub-screen 216, and a customized activity algorithm sub-screen 218 from which a user may review inputted and generated values to confirm correctness of the order to be place. In embodiments, model outputs on the review order page 212 may include target liver mass, activity at administration, calculated dose to the lungs, dose limit to the lungs, cumulative dose to the lungs, cumulative dose limit to the lungs, and/or a recommended number of radioactive compound microspheres for Y90 radioembolization (e.g., spheres). The user may utilize a Back button 220 to return to the previous order page screen 200A of FIG. 2 to edit an order input and/or selection. Alternatively, the user may select a Confirm Order Details button 222 to advance through the dosimetry portal 100 to a confirm order page screen 230 of FIG. 4 to confirm and place an order.

Figure 4:
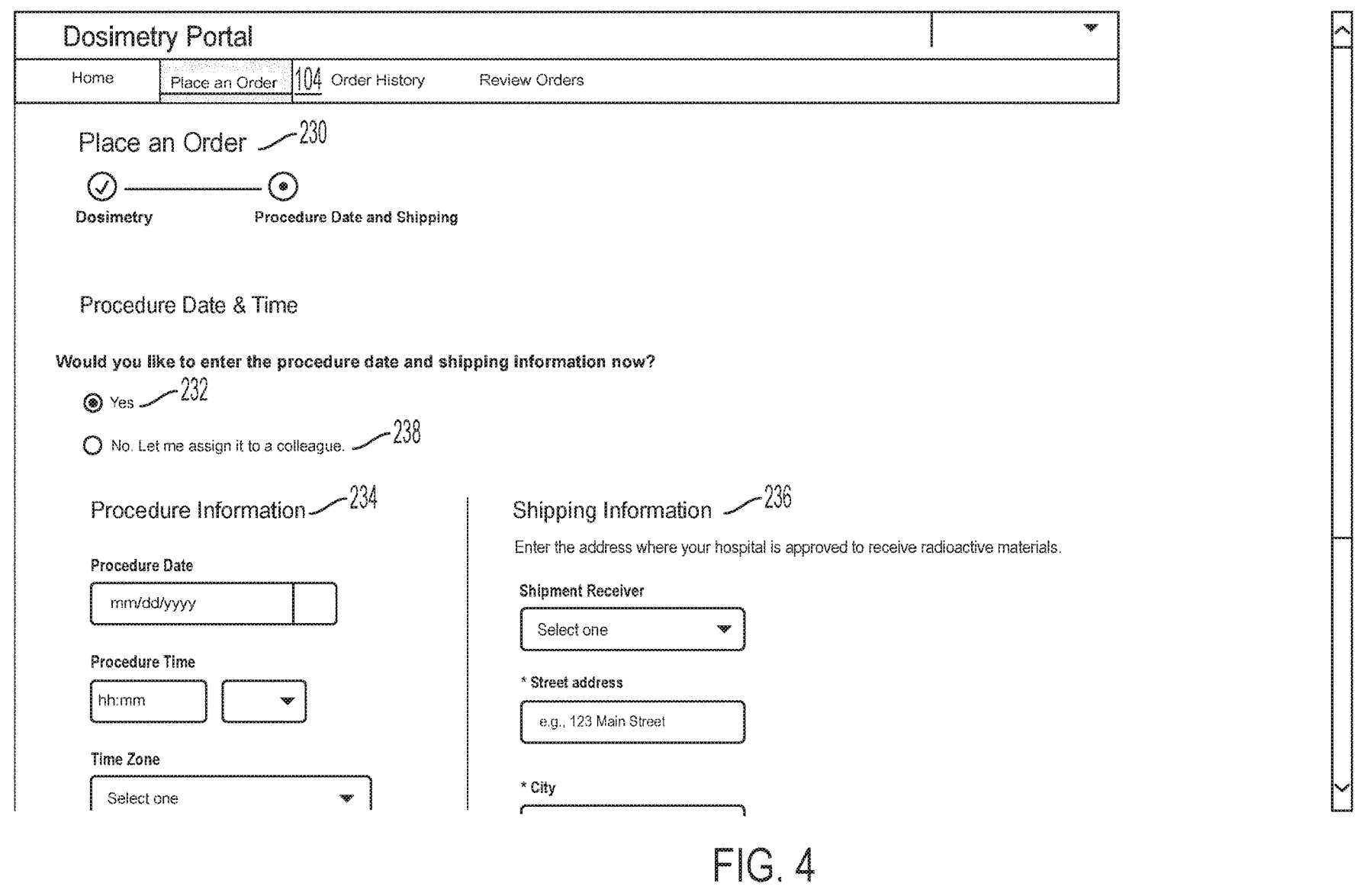

Referring to the confirm order page screen 230 of FIG. 4, a user may determine through selection of a Yes button 232 that the user is ready to enter the procedure date and shipping information to prepare for order placement. The user may enter procedure information into a Procedure Information sub-screen 234, such as procedure date, time, and time zone, and/or other pertinent procedure information such as a patient identifier and the like. The user may further enter shipping information in a Shipping Information sub-screen 236, such as a shipment address and shipment receiver information. In embodiments, the shipping information may be auto-populated or selected from a pre-configured drop-down menu.

Figure 5:
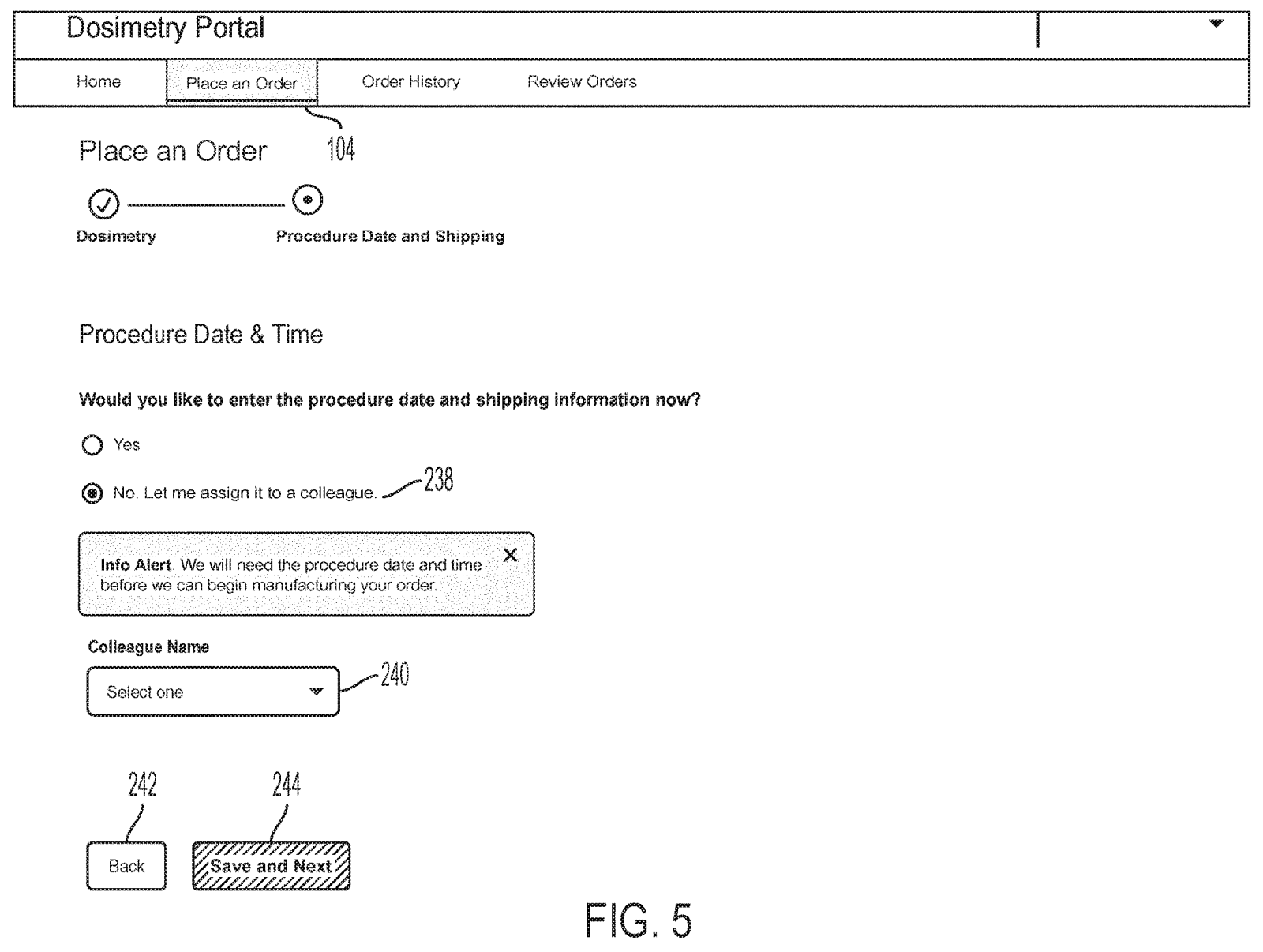

Referring to the confirm order page screen 230 of FIG. 5, a user may determine through selection of a No button 238 that the user is to assign shipping information input to another assigned user, selected from a drop down menu. In additional or alternative embodiments, the use of the No button 238 or through another assignment interface, the user may indicate that the user is not yet ready to enter the procedure date and shipping information to prepare for order placement and rather wishes to assign the order to appropriate review personnel for review and approval. In embodiments, the appropriate review personnel may approve the order and send the order back to the user for order placement, may place the order, may edit the order, and/or may send the order back to the user for editing. For one or more of such embodiments set forth above, the user may select the appropriate review personnel from a prepopulated personal name listing menu 240. The user may select a Back button 242 to return to a previous order screen as described above or select a Save and Next button 244 to send the order to the selected appropriate review personnel for review.

Referring to FIG. 6, a basic order page screen 200B as an alternative order page screen of the dosimetry portal 100 is shown. The user may use the order page screen 200B to submit one or more dosimetry inputs and select order details based on dosimetry and sphere recommendations as described herein on the order page screen 200B as a basic screen including one customized activity algorithm, such as the MIRD dosimetry calculation algorithm. The basic order page screen 200B may be used for a radioembolization procedure with a simply analysis. Alternatively, the user may select an Advanced Dosimetry button 250 to advance to an advanced order page screen 200C of FIG. 7. The advanced order page screen 200C may be used to evaluate the dosimetry models and sphere algorithms as described herein against one or more customized activity algorithms to view differences of end sphere amount and dosage recommendations per dosimetry selection algorithm and respective customized activity algorithm. The basic order page screen 200B and the advanced order page screen 200C may be linked for navigation and data transfer therebetween and with respect to a placed order.

Referring to FIG. 7, a first portion of the advanced order page screen 200C is shown. The first portion includes one or more dosimetry inputs for a respective plurality of customized activity algorithms, including for input into a MIRD Dosimetry Info sub-screen 252, a BSA Dosimetry Info sub-screen 254, and a Partition Dosimetry Info sub-screen 256. The inputs of the MIRD Dosimetry Info sub-screen 252, the BSA Dosimetry Info sub-screen 254, and the Partition Dosimetry Info sub-screen 256 are provided into respective customized activity algorithms to provide the calculated values in the respective customized activity sub-screens of, for example, a MIRD Calculate sub-screen 262, a BSA Calculate sub-screen 264, and a Partition Calculate sub-screen 266.

FIG. 8 shows a second portion of the advanced order page screen 200C in, for example, a scrolled down view, and including the MIRD Calculate sub-screen 262, the BSA Calculate sub-screen 264, and the Partition Calculate sub-screen 266, along with a Select Treatment Type option 270 to select as a non-limiting example a number of Bq per radioactive microsphere and a Recommendation Number of Spheres Selection Option 272 and may select between a set amount of recommendations of sphere amounts and dosages. Further included is a modification sub-screen 274 allowing for a user to select a desired amount of spheres values of millions, select an activity selection from a drop down list as may be calculated from the models of sub-screens 262, 264, and 266, input a dose modification as a percentage, and or insert as calculated based on the modified value (e.g., through a percentage or fractional value) a required activity value in units of gigabecquerel (GBq), which is a unit of radioactivity defined as the activity of a quantity of radioactive material in which a nucleus decays per second. An advanced button the advanced order page screen 200C may be used to show one or more different sphere selection algorithms.

The second portion of the advanced order page screen 200C of FIG. 8 further shows a Final Order Details sub-screen 276 including patient target dose in Gy units, Required Activity at Treatment in GBq units, Number of Spheres in Millions of units, GBq per sphere as a reference value, and a Date of expected Delivery. Once the Final Order Details of the Final Order Details sub-screen 276 are confirmed, the user may select an Order button 278 to continue with placing an order.

The user may advance to an Order Form screen 280 of FIG. 9, for example, that may be pre-populated with the calculated values and ready to be printed and/or further editing for submission to a manufacturer to generate the order. The Order Form screen 280 may further include an optional vial split section 282 such that a user may determine a percentage of split of the selected sphere amount and dosage among up to three different vials. The manufacturer may be able to receive the Order Form generated from the Order Form screen 280 to generate a printed bill of order based on the Order Form.

In embodiments, FIG. 10 illustrates an Approve Order screen 300 for appropriate review personnel selected to review an inputted order prior to submission of the order to the manufacturer to generate the order. The appropriate review use a Save button 302 to save information on the Approve Order screen 300.

FIG. 11 illustrates an Order History screen 400 in which a user may review a status of all orders, whether requiring approval, fulfilled, or in transit. A navigation sub-screen 402 on the Order History screen 400 may be utilized to navigate between screens to create, update, and approve orders and well as to see Order Status and History Information or to Fulfill Orders. In embodiments, the dosimetry portal 100 is configured to save, store, analyze, and/or report such as through the Order History screen 400 or another reporting interface information based on Order Status and History Information of one or more orders as described herein.

Referring to FIG. 12, a flow chart is shown of a process 1200 that utilizes the dosimetry portal screens of FIGS. 1-11 of the dosimetry portal 100 to generate an order as described herein, which may include the shipping and/or reviewer process embodiments as described herein. The process 1200 of FIG. 12 includes control scheme blocks for selection of dosimetry levels and sphere amounts of radioactive compounds for use in a radioembolization procedure for procedure planning. A user may sign into the dosimetry portal 100 with a user assigned security clearance level as described herein. In a block 1202, activity parameter information is input into the dosimetry portal 100 of a dosimetry selection tool 1312 (FIG. 13), which is described in greater detail further below. In embodiments, the activity parameter information may include a lung shunt fraction percentage value, an anticipated residual waste percentage value, a previous dose to lungs value, a desired dose to liver value and a target liver volume, such as shown in order page screen 200A, 200B, and 200C described herein.

In a block 1204, a customized activity is determined based on the activity parameter information of the block 1202 and one or more customized activity algorithms as described herein. The one or more customized activity algorithms may include at least one of a MIRD dosimetry calculation algorithm, a BSA dosimetry calculation algorithm, or a Partition dosimetry calculation algorithm, such as shown in order page screen 200A, 200B, and 200C described herein. In embodiments, the one or more customized activity algorithms may generate customized activity information include a target liver mass, activity at administration, a calculated dose to lungs, a dose limit to lungs, a cumulative dose to lungs, and a cumulative dose limit to lungs, and the customized activity may be based on the customized activity information.

In a block 1206, one or more sphere amount and dosage recommendations are generated based on the customized activity and one or more dosimetry selection algorithms as described herein. In embodiments, the one or more dosimetry selection algorithms to generate the one or more sphere amount and dosage recommendations may include at least one of an activity-per-sphere algorithm or an activity based on embolic load algorithm. The activity-per-sphere algorithm comprises division of the customized activity with a predetermined amount of spheres per activity unit as described herein. The activity based on embolic load algorithm may include use of a tissue volume input and a predetermined embolic load determination per cubic centimeter of tissue as described herein. For example, the predetermined embodiment load may include 20,000 spheres per cubic centimeter of tissue.

One of the one or more sphere amount and dosage recommendations is selected as a selected sphere amount and dosage recommendation. In embodiments, selecting the selected sphere amount and dosage recommendation may include selecting a desired radioactivity level per sphere and/or may include inputting a dose modification as a positive or negative percentage value, such as shown in the Order Details sub-screen 208 of FIG. 2. Further, also as shown in the Order Details sub-screen of FIG. 2, selecting the selected sphere amount and dosage recommendation may include splitting the selected sphere amount and dosage recommendation across a plurality of vials based on a percent differentiation per vial, the percent differentiation in total summing to 100% of the selected sphere amount and dosage recommendation. In embodiments, the plurality of vials may include a maximum of up to three vials.

In block 1208, a radioactive compound order for the radioembolization procedure is generated based on the customized activity and the selected sphere amount and dosage recommendation and placed such that the order is submitted to a manufacturer to fulfill. The process 200 may further include transmitting the radioactive compound order to a radioactive compound manufacturer for processing and order fulfillment. As a non-limiting example, this may occur through the confirm order page screen 230 of FIG. 4 when the Yes button 232 is selected and the user enters and submits procedure and shipping information. Alternatively, the process 200 may include assigning the radioactive compound order for review by an assigned personnel such that the radioactive compound order is transmitted to a radioactive compound manufacturer for processing and order fulfillment after approval by the assigned personnel. In embodiments, this may occur through the confirm order page screen 230 of FIG. 5 when the No button 238 is selected and a user assigns the order for review by a colleague as assigned personnel.

Figure 13:
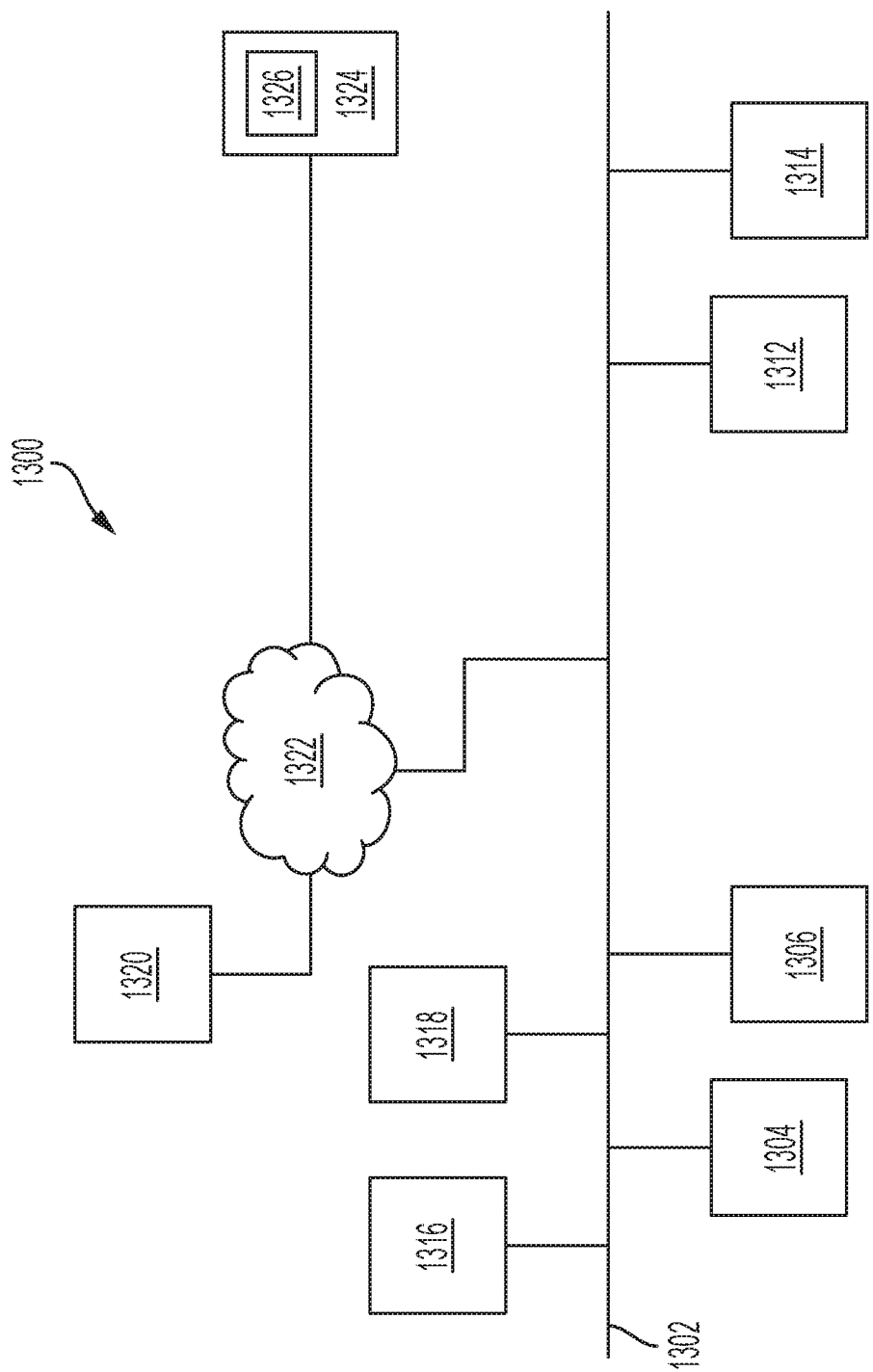
FIG. 13 schematically illustrates a system for implementing computer and software based methods to apply the process of FIG. 12 with the dosimetry portal of FIG. 1, according to one or more embodiments shown and described herein.

Referring to FIG. 13, a system 1300 for implementing a computer and software-based method to utilize the dosimetry selection software application tool embodiments described herein to determine one or more dosimetry and sphere selection recommendations for radioactive compounds for use with administered fluid to delivery through radioembolization delivery devices in a procedure is illustrated as being implemented along with using a graphical user interface (GUI) 1326 communicatively coupled to a computing device 1324, for example. The system 1300 includes a communication path 1302, one or more processors 1304, a memory component 1306, a dosimetry selection tool 1312, a storage or database 1314, a dosimetry selection algorithm 1316 configured to provide one or more dosimetry recommendations to the dosimetry selection tool 1312 as described herein, a network interface hardware 1318, a network 1322, a server 1320 that may include a cloud-based server, and the computing device 1224. The various components of the system 1300 and the interaction thereof will be described in detail below. In embodiments, the dosimetry selection tool 1312 may be directed to a flow software application tool, and the dosimetry selection algorithm 1316 may be directed to an optimization algorithm for flow rate determination for a radioembolization procedure for procedure planning as described in greater detail further below.

In some embodiments, the system 1300 is implemented using a wide area network (WAN) or network 1322, such as an intranet or the Internet. The computing device 1324 may include digital systems and other devices permitting connection to and navigation of the network. The computing device 1324 may be a laptop or desk computer or a smart mobile device such as a smartphone, a tablet, or a like portable handheld smart device. As a non-limiting example, the computing device 1324 may be a smartphone such as the iPhone® or a tablet such as the iPad®, both of which are commercially available from Apple, Inc. of Cupertino, CA The lines depicted in FIG. 13 indicate communication rather than physical connections between the various components.

As noted above, the system 1300 includes the communication path 1302. The communication path 1302 may be formed from any medium that is capable of transmitting a signal such as, for example, conductive wires, conductive traces, optical waveguides, or the like, or from a combination of mediums capable of transmitting signals. The communication path 1302 communicatively couples the various components of the system 1300. As used herein, the term "communicatively coupled" means that coupled components are capable of exchanging data signals with one another such as, for example, electrical signals via conductive medium, electromagnetic signals via air, optical signals via optical waveguides, and the like.

As noted above, the system 1300 includes the processor 1304. The processor 1304 can be any device capable of executing machine readable instructions. One or more algorithms described herein may be integrated directly into hardware, such as the processor 1304. The processor 1304 in embodiments may retrieve the algorithms and/or algorithm parameters from a database that may be local and/or stored in a cloud-server. Accordingly, the processor 1304 may be a controller, an integrated circuit, a microchip, a computer, or any other computing device. The processor 1304 is communicatively coupled to the other components of the system 1300 by the communication path 1302. Accordingly, the communication path 1302 may communicatively couple any number of processors with one another, and allow the modules coupled to the communication path 1302 to operate in a distributed computing environment. Specifically, each of the modules can operate as a node that may send and/or receive data.

As noted above, the system 1300 includes the memory component 1306 which is coupled to the communication path 1302 and communicatively coupled to the processor 1304. The memory component 1306 may be a non-transitory computer readable medium or non-transitory computer readable memory and may be configured as a nonvolatile computer readable medium. The memory component 1306 may comprise RAM, ROM, flash memories, hard drives, or any device capable of storing machine readable instructions such that the machine readable instructions can be accessed and executed by the processor 1304.

The machine readable instructions may comprise logic or algorithm(s) written in any programming language such as, for example, machine language that may be directly executed by the processor, or assembly language, object-oriented programming (OOP), scripting languages, microcode, etc., that may be compiled or assembled into machine readable instructions and stored on the memory component 1306. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components.

Still referring to FIG. 13, as noted above, the system 1300 comprises the display such as a GUI 1326 on a screen of the computing device 1324 for providing visual output such as, for example, information, graphical reports, messages, or a combination thereof. The display on the screen of the computing device 1324 is coupled to the communication path 1302 and communicatively coupled to the processor 1304. Accordingly, the communication path 1302 communicatively couples the display to other modules of the system 1300. The display can include any medium capable of transmitting an optical output such as, for example, a cathode ray tube, light emitting diodes, a liquid crystal display, a plasma display, or the like. Additionally, it is noted that the display or the computing device 1324 can include at least one of the processor 1304 and the memory component 1306. While the system 1300 is illustrated as a single, integrated system in FIG. 13, in other embodiments, the systems can be independent systems.

The system 1300 may comprise the dosimetry selection algorithm 1316 to compute and provide one or more dosimetry and sphere selection recommendations to the dosimetry selection tool 1312, as per one or more of the embodiments described herein. As will be described in further detail below, the processor 1304 may process the input signals received from the system modules and/or extract information from such signals. For example, in embodiments, the processor 1304 may execute instructions stored in the memory component 1306 to implement the processes described herein.

The system 1300 includes the network interface hardware 1318 for communicatively coupling the system 1300 with a computer network such as network 1322. The network interface hardware 1318 is coupled to the communication path 1302 such that the communication path 1302 communicatively couples the network interface hardware 1318 to other modules of the system 1300. The network interface hardware 1318 can be any device capable of transmitting and/or receiving data via a wireless network. Accordingly, the network interface hardware 1318 can include a communication transceiver for sending and/or receiving data according to any wireless communication standard. For example, the network interface hardware 1318 can include a chipset (e.g., antenna, processors, machine readable instructions, etc.) to communicate over wired and/or wireless computer networks such as, for example, wireless fidelity (Wi-Fi), WiMax, Bluetooth®, IrDA, Wireless USB, Z-Wave, ZigBee, or the like.

Still referring to FIG. 13, data from various applications running on the dosimetry selection tool 1312 can be provided from the computing device 1324 to the system 1300 via the network interface hardware 1318. The computing device 1324 can be any device having hardware (e.g., chipsets, processors, memory, etc.) for communicatively coupling with the network interface hardware 1318 and a network 1322.

The network 1322 can include any wired and/or wireless network such as, for example, wide area networks, metropolitan area networks, the Internet, an Intranet, satellite networks, or the like. Accordingly, the network 1322 can be utilized as a wireless access point to access one or more servers (e.g., a server 1320). The server 1320 and any additional servers generally include processors, memory, and chipset for delivering resources via the network 1322. Resources can include providing, for example, processing, storage, software, and information from the server 1320 to the system 1300 via the network 1322. Additionally, it is noted that the server 1320 and any additional servers can share resources with one another over the network 1322 such as, for example, via the wired portion of the network, the wireless portion of the network, or combinations thereof.

The embodiments of the dosimetry selection tool 1312 described herein through the dosimetry portal 100 permit users to calculate a required customized radioactivity as a customized activity for a Y90 radioembolization procedure for a particular patient set for a planned procedure as well as a desired amount of spheres and a dosage per sphere to obtain the customized activity. Furthermore, the selection of the desired amount of spheres may be split among separate vials for separate delivery to tissue and/or blood vessels.

The dosimetry platforms described herein offer a medium for physician and users to customize dosage per patient. Characteristics such as tumor vascularity, anatomy, cancer type, patient age, patient performance status, and the like, may be considered as factors in the selection of a desired amount of spheres with an selected activity per sphere to achieve a total customized activity based on dosimetry inputs and one or more algorithms as described herein. Users may input appropriate dosimetry information to view, evaluate, and compare several algorithms to determine an appropriate number of spheres or to use a predetermined activity per sphere value. After selection of an appropriate dosage and number of spheres for a patient, advanced dosimetry data may be imported into an ordering form to be sent to other personnel for review and/or approval or to a manufacturer for order processing and fulfillment.

It is contemplated and within the scope of this disclosure that the dosimetry selection tool 1312 may further be used for other radioactive materials and isolates, may include and be used for other embolics such as bland, scout dosing, chemo, and the like (e.g., chemoembolization), may be tailored to other sphere materials and delivery systems, may be directly integrated with imaging viewing and/or analysis software, and/or may be utilized across mobile to website platforms.

Further, and as a non-limiting example, during a radioembolization procedure, a determination of a flow rate of injection of the administered fluid including the spheres (e.g., particles) may affect a dispersion and the spheres themselves. The software application tools described herein may alternatively or additionally including algorithms directed to, based on input information, determine a recommended flow rate and probability of reflux with the recommended flow rate for a user that may be provided prior to and/or during a procedure in real-time. The software application tools may be provided in a separate application based platform, such as a mobile application ("app") or a web-based app, and/or may be an integrated part of a delivery device and/or system for a radioembolization procedure such that a display communicatively coupled to the delivery device may display the output information generated by the software application tools.

In embodiments, computational fluid dynamics analysis (CFD) may be used to determine the effect of flow rate on dispersion and particles during a radioembolization procedure. Further, travel of injected inappropriate particles may travel in retrograde as a reflux against the flow of blood and into adjoining vasculature and organs, which may negatively affect healthy tissue. The software application tools are configured to receipt one or more inputs to generate an output including a recommended flow rate based on the inputs and/or a probability of reflux based on the inputs and/or the recommended flow rate. Inputs may include particle characteristics such as geometry, size, density, and/or the like. Inputs may additionally or alternatively include clinical procedure planning inputs for the radioembolization procedure such as fluid type, catheter tip angle, blood flow rate, and/or the like. A flow software application tool may output an injection flow rate in milliliters/minute and/or a probability of reflux based on the one or more inputs and a calculating algorithm within the tool.

In an embodiment, during a scout dose procedure in preparation of the radioembolization procedure, a clinician may inject Technetium-99 (99Tc or Tc-99) into a vascular system to assess particle flow and delivery and may monitor and record clinically relevant information for use as the one or more inputs in the flow software application tool. Such information may be, for example, a catheter tip angle, a blood flow rate, and the like. The clinical may input the one or more inputs into the flow software application tool. The flow software application tool is configured to apply one or more algorithms as described herein to optimize flow rate and minimize reflux and, based on the one or more inputs, output one or more recommended flow rates and/or probability of reflux based on a recommended flow rate as selected by a clinician.

During the radioembolization procedure, a clinician may confirm via the flow software application tool a match between the procedure and prior clinician inputs, such as catheter tip angle, blood flow rate, and/or the like. Alternatively, the clinician may enter new one or more inputs into the flow software application tool to generate one or more updated flow rate recommendations and/or corresponding probabilities of reflux. The delivery device may then be configured to automatically, partially automatically, or manually inject particles at the selected flow rate recommendation into a patient.

Thus, the flow software application tool be configured to generate one or more flow rate recommendations for an optimal injection flow rate for radioembolization beads (e.g., spheres or particles) and to evaluate an associated probability of reflux based on one or more inputs and an optimization algorithm to optimize flow rate and minimize reflux. The optimization algorithm may be based on parameters and factors such as information, data, and/or other stored sub-algorithms directs to engineering fluid mechanics calculations, integrated clinical data, and/or advanced computational fluid dynamics simulations that leverage physics-based partial differential equations to describe a transport of Y90 radioembolization spheres through hepatic arteries of a patient. Such parameters and factors may be available to the optimization algorithm through data lookup tables, regression models, transfer functions, neural networks, and/or the like. The one or more inputs may be entered for pre-treatment planning or to provide a near real-time insight for adjustments to be made during the radioembolization procedure. The flow software application tool may be used in a technical setting in which a radioactivity and number for spheres for Y90 radioembolization, as described herein, is determined.

The systems described herein may a used for other radioactive materials and isotopes than those described herein, be used for other sphere materials and delivery systems as described herein, be configured to print out input and/or output or other clinical information for clinical documentation, be directly integrated with imaging viewing and/or analysis software, may utilized across application platforms such as a mobile app or web-based app, and/or be converted into a mechanical system.

Items Listing

Item 1. A method that is computer-implemented for selection of dosimetry levels and sphere amounts of radioactive compounds for use in a radioembolization procedure for procedure planning may include inputting activity parameter information into a dosimetry portal of a dosimetry selection tool; determining, via a processor, a customized activity based on the activity parameter information and one or more customized activity algorithms; generating one or more sphere amount and dosage recommendations based on the customized activity and one or more dosimetry selection algorithms; selecting one of the one or more sphere amount and dosage recommendations as a selected sphere amount and dosage recommendation; and generating, via the processor, a radioactive compound order for the radioembolization procedure based on the customized activity and the selected sphere amount and dosage recommendation.

Item 2. The method of item 1, further including transmitting the radioactive compound order to a radioactive compound manufacturer for processing and order fulfillment.

Item 3. The method of items 1 or 2, further including assigning the radioactive compound order for review by an assigned personnel such that the radioactive compound order is transmitted to a radioactive compound manufacturer for processing and order fulfillment after approval by the assigned personnel.

Item 4. The method of any of items 1 to 3, wherein the activity parameter information includes a lung shunt fraction percentage value, an anticipated residual waste percentage value, a previous dose to lungs value, a desired dose to liver value and a target liver volume.

Item 5. The method of any of items 1 to 4, wherein the one or more customized activity algorithms includes at least one of a MIRD dosimetry calculation algorithm, a BSA dosimetry calculation algorithm, or a Partition dosimetry calculation algorithm.

Item 6. The method of any of items 1 to 5, wherein: the one or more customized activity algorithms generate customized activity information comprising a target liver mass, activity at administration, a calculated dose to lungs, a dose limit to lungs, a cumulative dose to lungs, and a cumulative dose limit to lungs; and the customized activity is based on the customized activity information.

Item 7. The method of items 1 to 6, wherein the one or more dosimetry selection algorithms to generate the one or more sphere amount and dosage recommendations include at least one of an activity-per-sphere algorithm or an activity based on embolic load algorithm.

Item 8. The method of item 7, wherein the activity-per-sphere algorithm comprises division of the customized activity with a predetermined amount of spheres per activity unit.

Item 9. The method of item 7, wherein the activity based on embolic load algorithm comprises use of a tissue volume input and a predetermined embolic load determination per cubic centimeter of tissue.

Item 10. The method of item 9, wherein the predetermined embodiment load comprises 20,000 spheres per cubic centimeter of tissue.

Item 11. The method of any of items 1 to 10, wherein selecting the selected sphere amount and dosage recommendation further includes selecting a desired radioactivity level per sphere.

Item 12. The method of any of items 1 to 11, wherein selecting the selected sphere amount and dosage recommendation further includes inputting a dose modification as a positive or negative percentage value.

Item 13. The method of any of items 1 to 12, wherein selecting the selected sphere amount and dosage recommendation further includes splitting the selected sphere amount and dosage recommendation across a plurality of vials based on a percent differentiation per vial, the percent differentiation in total comprising 100% of the selected sphere amount and dosage recommendation.

Item 14. The method of item 13, wherein the plurality of vials includes a maximum of three vials.

Item 15. The method of any of items 1 to 14, wherein the dosimetry portal is configured to provide for data collaboration among a plurality of users such that the plurality of users are granted access rights to view at least one of a first draft order or one or more radioactive compound orders, a user is assigned one of a plurality of security clearance levels, and the plurality of security clearance levels include at least one of a basic security clearance level or an advanced security clearance level providing a user with a greater amount of access rights than the basic security clearance level.

Item 16. The method of item 15, wherein the basic security clearance level is configured to allow a first user to create the first draft order, and the advanced security clearance level is configured to permit a second user to review and approve the first draft order.

Item 17. A system for selection of dosimetry levels and sphere amounts of radioactive compounds for use in a radioembolization procedure for procedure planning may include a dosimetry selection tool including a dosimetry portal and a graphical user interface, and a processor communicatively coupled to a dosimetry selection tool and a non-transitory computer storage medium, wherein the non-transitory computer storage medium stores instructions that, when executed by the processor, cause the processor to: receive, via the graphical user interface, an input of activity parameter information into the dosimetry portal of the dosimetry selection tool; determine, via the processor, a customized activity based on the activity parameter information and one or more customized activity algorithms; generate, via the processor, one or more sphere amount and dosage recommendations based on the customized activity and one or more dosimetry selection algorithms; receive, via the graphical user interface, a selection of one of the one or more sphere amount and dosage recommendations as a selected sphere amount and dosage recommendation; and generate, via a processor, a radioactive compound order for the radioembolization procedure based on the customized activity and the selected sphere amount and dosage recommendation.

Item 18. The system of item 17, further including instructions that, when executed by the processor, cause the processor to transmit the radioactive compound order to a radioactive compound manufacturer for processing and order fulfillment.

Item 19. The system of items 17 or 18, further including instructions that, when executed by the processor, cause the processor to assign the radioactive compound order for review by an assigned personnel such that the radioactive compound order is transmitted to a radioactive compound manufacturer for processing and order fulfillment after approval by the assigned personnel.

Item 20. The system of any of items 17 to 19, wherein the one or more customized activity algorithms includes at least one of a MIRD dosimetry calculation algorithm, a BSA dosimetry calculation algorithm, or a Partition dosimetry calculation algorithm.

Item 21. The system of any of items 17 to 20, wherein the one or more dosimetry selection algorithms to generate the one or more sphere amount recommendations includes at least one of an activity-per-sphere algorithm or an activity based on embolic load algorithm.

Item 22. The system of any of items 17 to 21, further including instructions that, when executed by the processor, cause the processor to receive, via the graphical user interface, a percentage split of the selected sphere amount and dosage recommendation across a plurality of vials.

Item 23. A system for flow rate determination for a radioembolization procedure for procedure planning may include a delivery device, a flow software application tool including a graphical user interface to receive one or more inputs related to the radioembolization procedure, and a processor communicatively coupled to the delivery device, the flow software application tool, and a non-transitory computer storage medium, wherein the non-transitory computer storage medium stores instructions that, when executed by the processor, cause the processor to: receive, via the graphical user interface, the one or more inputs related to the radioembolization procedure; determine, via the processor, one or more flow rate recommendations based on the one or more inputs and one or more optimization algorithms; generate, via the processor, one or more corresponding probabilities of reflux based on the one or more flow rate recommendations; receive, via the graphical user interface, a selection of one of the one or more flow rate recommendations as a selected flow rate recommendation; and use the delivery device to deliver Y90 radioembolization spheres for the radioembolization procedure based on the selected flow rate recommendation.

It is noted that the terms "substantially" and "about" and "approximately" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method that is computer-implemented for selection of dosimetry levels and sphere amounts of radioactive compounds for use in a radioembolization procedure for procedure planning, the method comprising:
   inputting activity parameter information into a dosimetry portal of a dosimetry selection tool;
   determining, via a processor, a customized activity based on the activity parameter information and one or more customized activity algorithms;
   generating at least two sphere amount and dosage recommendations based on the customized activity and one or more dosimetry selection algorithms;
   selecting one of the at least two sphere amount and dosage recommendations as a selected sphere amount and dosage recommendation;
   modifying the selected sphere amount and dosage recommendation as a modified selected sphere amount and dosage recommendation; and
   generating, via the processor, a radioactive compound order for the radioembolization procedure based on the customized activity and the modified selected sphere amount and dosage recommendation.

2. The method of claim 1, further comprising transmitting the radioactive compound order to a radioactive compound manufacturer for processing and order fulfillment.

3. The method of claim 1, further comprising assigning the radioactive compound order for review by an assigned personnel such that the radioactive compound order is transmitted to a radioactive compound manufacturer for processing and order fulfillment after approval by the assigned personnel.

4. The method of claim 1, wherein the activity parameter information comprises a lung shunt fraction percentage value, an anticipated residual waste percentage value, a previous dose to lungs value, a desired dose to liver value and a target liver volume.

5. The method of claim 1, wherein the one or more customized activity algorithms comprises at least one of a MIRD dosimetry calculation algorithm, a BSA dosimetry calculation algorithm, or a Partition dosimetry calculation algorithm.

6. The method of claim 1, wherein:
the one or more customized activity algorithms generate customized activity information comprising a target liver mass, activity at administration, a calculated dose to lungs, a dose limit to lungs, a cumulative dose to lungs, and a cumulative dose limit to lungs; and
the customized activity is based on the customized activity information.

7. The method of claim 1, wherein the one or more dosimetry selection algorithms to generate the at least two sphere amount and dosage recommendations comprises at least one of an activity-per-sphere algorithm or an activity based on embolic load algorithm.

8. The method of claim 7, wherein the activity-per-sphere algorithm comprises division of the customized activity with a predetermined amount of spheres per activity unit.

9. The method of claim 7, wherein the activity based on embolic load algorithm comprises use of a tissue volume input and a predetermined embolic load determination per cubic centimeter of tissue.

10. The method of claim 9, wherein the predetermined embolic load determination comprises 20,000 spheres per cubic centimeter of tissue.

11. The method of claim 1, wherein selecting the selected sphere amount and dosage recommendation further comprises selecting a desired radioactivity level per sphere.

12. The method of claim 1, wherein selecting the selected sphere amount and dosage recommendation further comprises inputting a dose modification as a positive or negative percentage value.

13. The method of claim 1, wherein selecting the selected sphere amount and dosage recommendation further comprises splitting the selected sphere amount and dosage recommendation across a plurality of vials based on a percent differentiation per vial, the percent differentiation in total comprising 100% of the selected sphere amount and dosage recommendation.

14. The method of claim 13, wherein the plurality of vials comprises a maximum of three vials.

15. The method of claim 1, wherein:
the dosimetry portal is configured to provide for data collaboration among a plurality of users such that the plurality of users are granted access rights to view at least one of a first draft order or one or more radioactive compound orders;
a user is assigned one of a plurality of security clearance levels; and
the plurality of security clearance levels include at least one of a basic security clearance level or an advanced security clearance level providing a user with a greater amount of access rights than the basic security clearance level.

16. The method of claim 15, wherein the basic security clearance level is configured to allow a first user to create the first draft order, and the advanced security clearance level is configured to permit a second user to review and approve the first draft order.

17. A system for selection of dosimetry levels and sphere amounts of radioactive compounds for use in a radioembolization procedure for procedure planning, the system comprising:
a dosimetry selection tool including a dosimetry portal and a graphical user interface; and
a processor communicatively coupled to the dosimetry selection tool and a non-transitory computer storage medium, wherein the non-transitory computer storage medium stores instructions that, when executed by the processor, cause the processor to:
receive, via the graphical user interface, an input of activity parameter information into the dosimetry portal of the dosimetry selection tool;
determine, via the processor, a customized activity based on the activity parameter information and one or more customized activity algorithms;
generate, via the processor, at least two sphere amount and dosage recommendations based on the customized activity and one or more dosimetry selection algorithms;
receive, via the graphical user interface, a selection of one of the at least two sphere amount and dosage recommendations as a selected sphere amount and dosage recommendation;
modify the selected sphere amount and dosage recommendation as a modified selected sphere amount and dosage recommendation; and
generate, via the processor, a radioactive compound order for the radioembolization procedure based on the customized activity and the modified selected sphere amount and dosage recommendation.

18. The system of claim 17, further comprising instructions that, when executed by the processor, cause the processor to transmit the radioactive compound order to a radioactive compound manufacturer for processing and order fulfillment.

19. The system of claim 17, further comprising instructions that, when executed by the processor, cause the processor to assign the radioactive compound order for review by an assigned personnel such that the radioactive compound order is transmitted to a radioactive compound manufacturer for processing and order fulfillment after approval by the assigned personnel.

20. The system of claim 17, wherein the one or more customized activity algorithms comprises at least one of a MIRD dosimetry calculation algorithm, a BSA dosimetry calculation algorithm, or a Partition dosimetry calculation algorithm.

21. The system of claim 17, wherein the one or more dosimetry selection algorithms to generate the at least two sphere amount recommendations comprises at least one of an activity-per-sphere algorithm or an activity based on embolic load algorithm.

22. The system of claim 17, further comprising instructions that, when executed by the processor, cause the processor to receive, via the graphical user interface, a percentage split of the selected sphere amount and dosage recommendation across a plurality of vials.

23. A system for flow rate determination for a radioembolization procedure for procedure planning, the system comprising:

a delivery device;

a flow software application tool including a graphical user interface to receive one or more inputs related to the radioembolization procedure; and a processor communicatively coupled to the delivery device, the flow software application tool, and a non-transitory computer storage medium, wherein the non-transitory computer storage medium stores instructions that, when executed by the processor, cause the processor to:

receive, via the graphical user interface, the one or more inputs related to the radioembolization procedure;

determine, via the processor, one or more flow rate recommendations based on the one or more inputs and one or more optimization algorithms;

generate, via the processor, one or more corresponding probabilities of reflux based on the one or more flow rate recommendations;

receive, via the graphical user interface, a selection of one of the one or more flow rate recommendations as a selected flow rate recommendation; and use the delivery device to deliver Y90 radioembolization spheres for the radioembolization procedure based on the selected flow rate recommendation.

* * * * *